(12) United States Patent
Miyata et al.

(10) Patent No.: US 6,224,727 B1
(45) Date of Patent: May 1, 2001

(54) NO$_x$ SENSOR

(75) Inventors: Shigeru Miyata; Masashi Ando; Hiroshi Inagaki, all of Aichi; Noboru Ishida, Gifu; Takafumi Oshima, Aichi, all of (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/050,079

(22) Filed: Mar. 30, 1998

(30) Foreign Application Priority Data

Mar. 28, 1997 (JP) .................................................... 9-077680

(51) Int. Cl.$^7$ .................................................. G01N 27/26
(52) U.S. Cl. ............................ 204/425; 204/426; 205/781
(58) Field of Search ...................................... 504/421–429

(56) References Cited

U.S. PATENT DOCUMENTS

| | | | |
|---|---|---|---|
| 4,272,329 | * 6/1981 | Hetrick et al. | 204/425 |
| 4,502,939 | * 3/1985 | Holfelder et al. | 204/426 |
| 4,722,779 | * 2/1988 | Yamada et al. | 204/425 |
| 4,836,906 | * 6/1989 | Yamada et al. | 204/425 |
| 4,859,307 | * 8/1989 | Nishizawa et al. | 204/426 |
| 5,288,375 | 2/1994 | Logothetis et al. . | |
| 5,505,837 | 4/1996 | Friese et al. . | |
| 5,672,811 | * 9/1997 | Kato et al. | 204/426 |

FOREIGN PATENT DOCUMENTS

| | | |
|---|---|---|
| 0 517 366 | 12/1992 | (EP) . |
| 0 678 740 | 10/1995 | (EP) . |
| 0 678 740 A1 | 10/1995 | (EP) . |
| 0 791 826 | 8/1997 | (EP) . |
| 0 810 430 | 12/1997 | (EP) . |
| 95/30146 | 11/1995 | (WO) . |

\* cited by examiner

*Primary Examiner*—T. Tung
(74) *Attorney, Agent, or Firm*—Sughrue, Mion, Zinn, Macpeak & Seas, PLLC

(57) ABSTRACT

An NO$_x$ sensor capable of accurately determining the concentration of NO$_x$ contained in a gas to be analyzed (measurement gas) using a simple circuit. The NO$_x$ sensor includes a first measurement space and a second measurement space. The first measurement space communicates with the measurement gas via a first diffusion controlling layer, and the second measurement space communicates with the first measurement space via a second diffusion controlling layer. A first pumping current $I_{P1}$ is controlled such that an output from a Vs cell is used as a reference voltage $V_{C0}$ to control the amount of oxygen flowing into the second measurement space at a constant level. A constant voltage is applied to the second pumping cell so as to decompose the NO$_x$ component of the measurement gas contained in the second measurement space, and to pump out the resulting oxygen from the second measurement space. Accordingly, the concentration of NO$_x$ contained in the measurement gas can be obtained from second pumping current $I_{P2}$. The electrode of the Vs cell located on the side of the first measurement space is formed around the periphery of or on a portion of the diffusion controlling layer of the Vs cell. As a result, the amount of oxygen flowing from the first measurement space into the second measurement space can be accurately determined by means of the Vs cell. Also, the NO$_x$ concentration can be accurately determined without the need for compensation.

3 Claims, 7 Drawing Sheets

$NO_x$ SENSOR

FIELD OF THE INVENTION

The present invention relates to an $NO_x$ sensor for measuring the concentration of nitrogen oxides, or harmful emissions, contained in exhaust gases from various combustion apparatus, including internal combustion engines.

BACKGROUND OF THE INVENTION $NO_x$ sensors for measuring the concentration of nitrogen oxides ($NO_x$) contained in gases to be analyzed (hereinafter called "a measurement gas") are disclosed, for example, in European Patent Application Laid-Open No. 0678740A1 and SAE Paper No. 960334, pp. 137–142, 1996. Such conventional $NO_x$ sensors are composed of oxygen ion conductive solid electrolyte layers that form a first measurement space and a second measurement space. The first measurement space communicates with a measurement gas via a first diffusion controlling layer, and the second measurement space communicates with the first measurement space via a second diffusion controlling layer. Furthermore, the solid electrolyte layer of the first measurement space is sandwiched between porous electrodes so as to form a first oxygen pumping cell and an oxygen concentration measuring cell. Also, the solid electrolyte layer of the second measurement space is sandwiched between porous electrodes so as to form a second oxygen pumping cell.

In the thus configured $NO_x$ sensor, the first oxygen pumping cell is energized so that an output voltage from the oxygen concentration measuring cell achieves a predetermined value, to thereby pump out oxygen from the first measurement space and thus control the concentration of oxygen in the first measurement space to a constant level. At the same time, a constant voltage is applied to the second oxygen pumping cell to thereby pump out oxygen from the second measurement space. As a result, the $NO_x$ concentration of the measurement gas can be obtained by measuring the current flowing through the second oxygen pumping cell (hereinafter referred to as "second pumping current").

A measurement gas, e.g., exhaust from an internal combustion engine or the like, contains gas components other than $NO_x$, such as oxygen, carbon monoxide and carbon dioxide. Thus, in the aforementioned $NO_x$ sensor, current (hereinafter referred to as "first pumping current") is first applied to the first oxygen pumping cell to thereby pump out most of the oxygen from a measurement gas contained in the first measurement space. Then, in the second measurement space into which the oxygen-removed measurement gas flows, $NO_x$ contained in the measurement gas is decomposed into nitrogen and oxygen by means of the catalyzing function of the second oxygen pumping cell. The thus generated oxygen is then pumped out from the second measurement space. Thus, the $NO_x$ concentration of the measurement gas can be obtained by measuring the second pumping current without being affected by other gas components contained in the measurement gas.

In order to accurately measure the $NO_x$ concentration using the above described $NO_x$ sensor, the $NO_x$ sensor must be heated to a predetermined activation temperature (for example, 800° C. or higher) so as to activate the pumping cells. Accordingly, the $NO_x$ sensor is provided with a heater, and current applied to the heater is controlled so as to control the temperature of the $NO_x$ sensor at a predetermined level.

However, in a conventional $NO_x$ sensor, the $NO_x$ concentration obtained from the second pumping current must be appropriately compensated in order to provide an accurate measurement. This requires a complex signal processing system, with a resulting increase in the cost of the sensing apparatus. The above noted problems are described in detail below.

According to the design concept of a conventional $NO_x$ sensor, oxygen is pumped out from the first measurement space using the first oxygen pumping cell so as to control the measurement gas contained in the first measurement space at a very low oxygen concentration level. As a result, the measurement gas flowing into the second measurement space contains substantially $NO_x$ only. By decomposing the measurement gas into nitrogen and oxygen by means of the catalyzing function of the second oxygen pumping cell, the $NO_x$ concentration can be obtained from the second pumping current flowing through the second oxygen pumping cell.

However, in actuality, if the first oxygen pumping cell is controlled so that the concentration of oxygen contained in the first measurement space becomes substantially zero (theoretically, a partial pressure of about $10^{-9}$ atm), the $NO_x$ concentration cannot be obtained from the second pumping current. Thus, in order to measure the $NO_x$ concentration at a relatively high detection sensitivity using a conventional $NO_x$ sensor, the first oxygen pumping cell must be controlled such that the concentration of oxygen contained in the first measurement space becomes as low as about 1000 ppm.

A reason has been proposed as to why the $NO_x$ concentration cannot be obtained at a good detection sensitivity when the concentration of oxygen in the first measurement space is controlled to be substantially zero. Namely, as a result of controlling the first pumping current, the $NO_x$ component of a measurement gas contained in the first measurement space is decomposed. Consequently, the measurement gas flowing into the second measurement space does not contain $NO_x$ in an amount that is the same as that contained in the actual measurement gas to be analyzed.

Accordingly, when the $NO_x$ concentration is obtained from the second pumping current while the first oxygen pumping cell is controlled such that the concentration of oxygen contained in the first measurement space becomes as low as about 1000 ppm, the second pumping current varies in accordance with the $NO_x$ concentration of the measurement gas. However, the second pumping current is also affected by the oxygen concentration of the measurement gas. This is because the measurement gas flowing from the first measurement space into the second measurement space contains not only $NO_x$ but also oxygen. As a result, conventional $NO_x$ sensors fail to indicate the actual $NO_x$ concentration. This is because the $NO_x$ concentration thus obtained is affected by the oxygen concentration of the measurement gas present around the $NO_x$ sensor.

This problem can be solved, for example, by measuring the oxygen concentration of the measurement gas present around the $NO_x$ sensor based on the first pumping current and compensating the $NO_x$ concentration thus obtained in accordance with the measured oxygen concentration. That is, the first pumping current is controlled so that the concentration of oxygen contained in the first measurement space is maintained at a constant level. Also, the value of the first pumping current is proportional to the oxygen concentration of the measurement gas present around the $NO_x$ sensor. Thus, by obtaining the oxygen concentration of the ambient atmosphere from the first pumping current and thereby compensating the measured $NO_x$ concentration, an accurate $NO_x$ concentration can be obtained.

However, in order to compensate the measured $NO_x$ concentration by obtaining the oxygen concentration of the measurement gas as described above, additional compensation means are required which leads to an increase in the cost of the sensing apparatus. The present invention has been accomplished in view of the above described problems of the prior art.

SUMMARY OF THE INVENTION

It is thereof an object of the present invention to provide an $NO_x$ sensor capable of accurately measuring the $NO_x$ concentration of a measurement gas using a relatively simple circuit, and without the need for compensating the $NO_x$ concentration obtained from the second pumping current in accordance with the oxygen concentration of the measurement gas.

The above objectives of the present invention have been achieved by providing an $NO_x$ sensor for measuring the $NO_x$ concentration of a measurement gas comprising a first measurement space and a second measurement space. The first measurement space includes a first oxygen pumping cell and an oxygen concentration measuring cell, and communicates with the measurement gas via a first diffusion controlling layer. The first oxygen pumping cell comprises an oxygen ion conductive solid electrolyte layer and porous electrodes disposed on opposite surfaces of the oxygen ion conductive solid electrolyte layer. The oxygen concentration measuring cell comprises an oxygen ion conductive solid electrolyte layer and porous electrodes disposed on opposite surfaces of the oxygen ion conductive solid electrolyte layer. The second measurement space includes a second oxygen pumping cell and communicates with the first measurement space via a second diffusion controlling layer. The second oxygen pumping cell comprises an oxygen ion conductive solid electrolyte layer and porous electrodes disposed on opposite surfaces of the oxygen ion conductive solid electrolyte layer. Oxygen is pumped out from the first measurement space by means of the first oxygen pumping cell such that an output voltage from the oxygen concentration measuring cell is maintained at a constant value. A constant voltage is applied to the second oxygen pumping cell in a polarity such that oxygen is pumped out from the second measurement space, whereby the concentration of $NO_x$ contained in the measurement gas can be determined by measuring the current flowing through the second oxygen pumping cell. Preferably, the oxygen concentration measuring cell is disposed in a position such that the amount of oxygen contained in the measurement gas flowing from the first measurement space into the second measurement space via the second diffusion controlling layer can be determined without being affected by the distribution of oxygen within the first measurement space.

DESCRIPTION OF THE PREFERRED EMBODIMENTS

Figure 1:
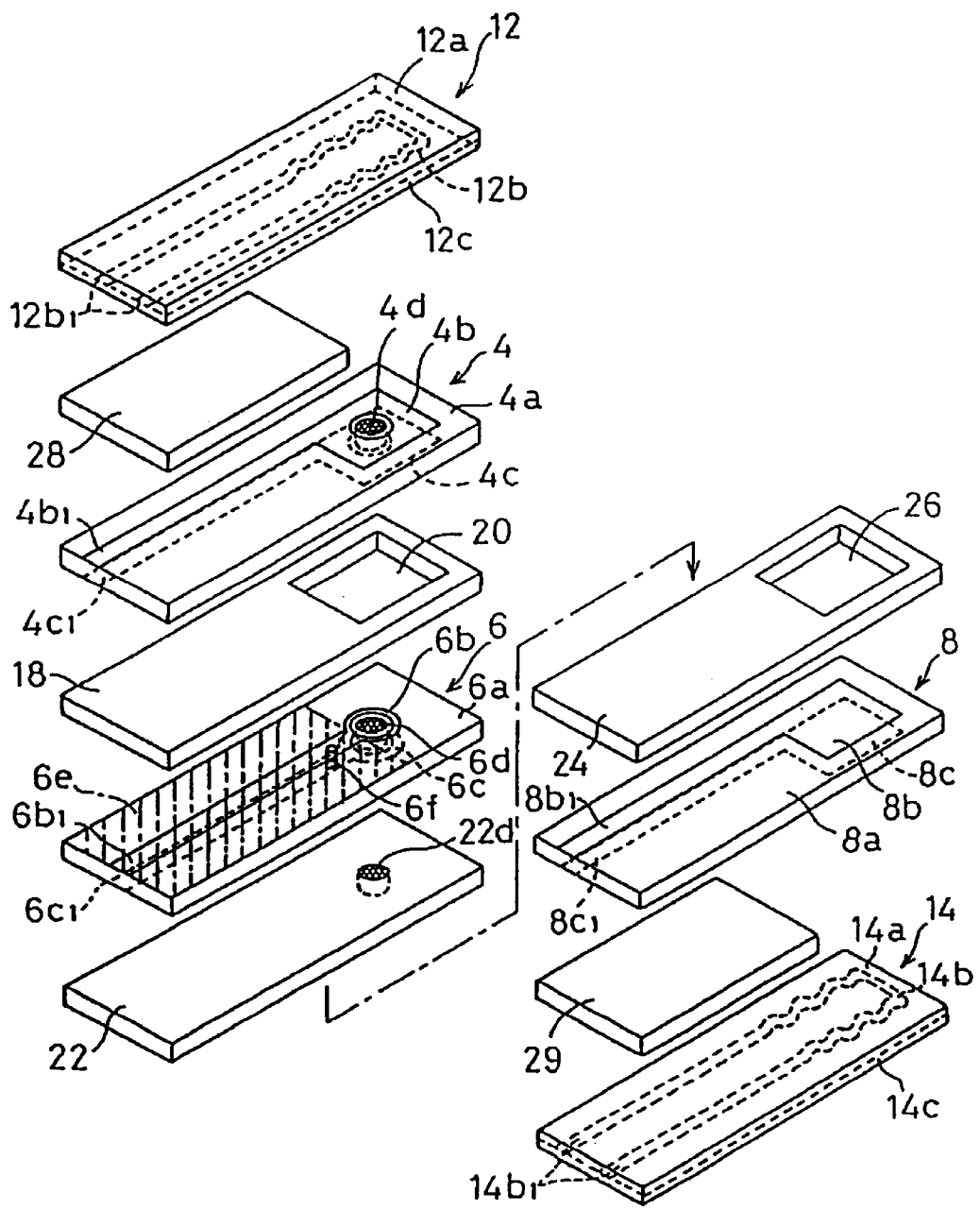
FIG. 1 is an exploded perspective view showing the structure of an $NO_x$ sensor according to an embodiment of the present invention.

In the $NO_x$ sensor of the present invention, the oxygen concentration measuring cell is preferably disposed in a position such that the amount of oxygen contained in the measurement gas flowing from the first measurement space into the second measurement space via the second diffusion controlling layer can be determined without being affected by the distribution of oxygen within the first measurement space. This configuration is employed for the reason described below.

In a conventional $NO_x$ sensor, the oxygen concentration measuring cell is disposed so as to determine the concentration of oxygen contained in the first measurement space. By contrast, in the $NO_x$ sensor of the present invention, the oxygen concentration measuring cell is disposed so as to determine the amount of oxygen flowing from the first measurement space into the second measurement space. Thus, the oxygen concentration of the measurement gas flowing into the second measurement space can be accurately determined. Accordingly, the first oxygen pumping cell can be controlled such that the oxygen concentration of the measurement gas flowing into the second measurement space becomes substantially zero.

As discussed above, in a conventional $NO_x$ sensor, if the first oxygen pumping cell is controlled such that the concentration of oxygen contained in the first measurement space becomes substantially zero (theoretically, a partial pressure of about $10^{-9}$ atm), the $NO_x$ concentration cannot be accurately determined from the second pumping current. Thus, the first oxygen pumping cell is controlled so that the concentration of oxygen contained in the first measurement space becomes as low as about 1000 ppm. The cause for this failure in the ability to accurately determine the $NO_x$ concentration has been considered to be as follows. Namely, if the first oxygen pumping cell is controlled such that the concentration of oxygen contained in the first measurement space becomes substantially zero, the $NO_x$ component of the measurement gas contained in the first measurement space is decomposed. Consequently, the measurement gas flowing into the second measurement space does not contain $NO_x$ in the same amount as contained in the actual gas to be analyzed.

The present inventors studied the above described phenomena and discovered the following. In a conventional $NO_x$ sensor, the electrode of the oxygen concentration measuring cell located on the side of the first measurement space has a relatively large size so as to detect the concentration of oxygen contained in the first measurement space by means of the oxygen concentration measuring cell. Consequently, the average concentration of oxygen contained in the first measurement space can be determined, but the concentration of oxygen contained in the measurement gas flowing from the first measurement space into the second measurement space cannot be determined. That is, because an external measurement gas flows into the first measurement space via the first diffusion controlling layer and because oxygen is pumped out from the incoming measurement gas by means of the first oxygen pumping cell, the distribution of oxygen within the first measurement space becomes nonuniform. As a result, in a conventional $NO_x$ sensor, the concentration of oxygen contained in the measurement gas flowing from the first measurement space into the second measurement space cannot be determined by the oxygen concentration measuring cell.

Thus, in the present invention, the oxygen concentration measuring cell is disposed so as to determine the amount of oxygen flowing from the first measurement space into the second measurement space rather than the concentration of oxygen contained in the first measurement space. As a result, the amount of oxygen flowing from the first measurement space to the second measurement space can be accurately determined by means of the oxygen concentration measuring cell.

According to the present invention, by controlling the current applied to the first oxygen pumping cell, the amount of oxygen flowing from the first measurement space into the second measurement space is controlled to substantially zero, so that the measurement gas contained in the second measurement space contains only an $NO_x$ component in the same amount as contained in the external measurement gas. Thus, the $NO_x$ concentration can be accurately determined from the second pumping current.

Because the $NO_x$ concentration can be accurately determined from the second pumping current flowing through the second oxygen pumping cell, the thus obtained $NO_x$ concentration does not need to be compensated in accordance with the concentration of oxygen contained in the measurement gas. Accordingly, the signal processing system for determining the $NO_x$ concentration can be implemented in a simple configuration, and thus the sensing apparatus cost can be reduced.

As in the case of the aforementioned conventional $NO_x$ sensor, the $NO_x$ sensor of the present invention preferably includes heaters for heating the cells to a predetermined activation temperature in order to accurately measure the $NO_x$ concentration.

When heaters for heating and temperature control are provided, the following structure is preferably employed. The first oxygen pumping cell, the oxygen concentration measuring cell and the second oxygen pumping cell are respectively formed of sheet-like solid electrolyte layers. The solid electrolyte layers are arranged in a laminate such that the solid electrolyte layer constituting the first oxygen pumping cell and the solid electrolyte layer constituting the second oxygen pumping cell are arranged as the outer layers of the laminate. A predetermined gap is provided between these outer solid electrolyte layers and the inner solid electrolyte layer or layers, to thereby define first and second measurement spaces. A sheet-like heater substrate having a heater is disposed on both sides of the solid electrolyte layers in the laminating direction such that a predetermined gap is provided between the heater substrate and the solid electrolyte layers. Furthermore, the first diffusion controlling layer is formed in the solid electrolyte layer having the first oxygen pumping cell at a position opposite a central portion of the heater formed in the heater substrate.

According to the $NO_x$ sensor of the present invention as configured above, the solid electrolyte layer constituting the oxygen concentration measuring cell is interposed between the solid electrolyte layer constituting the first oxygen pumping cell and the solid electrolyte layer constituting the second oxygen pumping cell, and the heater substrate is disposed on both sides of the layered solid electrolytes in the laminating direction. Accordingly, by controlling current applied to the heaters, the cells can be readily controlled to a predetermined temperature. Also, the measurement gas flowing into the first measurement space through the first diffusion controlling layer and flowing further into the second measurement space can be heated to a predetermined temperature. Thus, temperature variations among the cells are less likely to occur, and the cells are less sensitive to the temperature of the measurement gas. Therefore, the accuracy of the $NO_x$ concentration measurement can be improved.

Preferably, the second diffusion controlling layer is formed so as to at least partially overlap the first diffusion controlling layer when the $NO_x$ sensor is projected in the laminating direction. This enables more reliable temperature control of the measurement gas flowing from the first measurement space to the second measurement space to a target temperature. Thus, the accuracy of the $NO_x$ concentration measurement can be improved.

Preferably, the oxygen concentration measuring cell is formed around the periphery of the second diffusion controlling layer. Alternatively, the second diffusion controlling layer is formed of a porous solid electrolyte layer capable of controlling the diffusion of the measurement gas, and the electrode of the oxygen concentration measuring cell located on the side of the first measurement space is formed on the second diffusion controlling layer. Thus, in this embodiment of the present invention, the oxygen concentration measuring cell is disposed in a position such that the amount of oxygen contained in the measurement gas flowing from the first measurement space into the second measurement space can be measured without being affected by the distribution of oxygen within the first measurement space. This enables accurate measurement of the amount of oxygen contained in the measurement gas flowing from the first measurement space into the second measurement space. Accordingly, the above described effects can be reliably achieved.

Various embodiments of the present invention are described below with reference to the drawings. However, the present invention should not be construed as being limited thereto.

Figure 2:
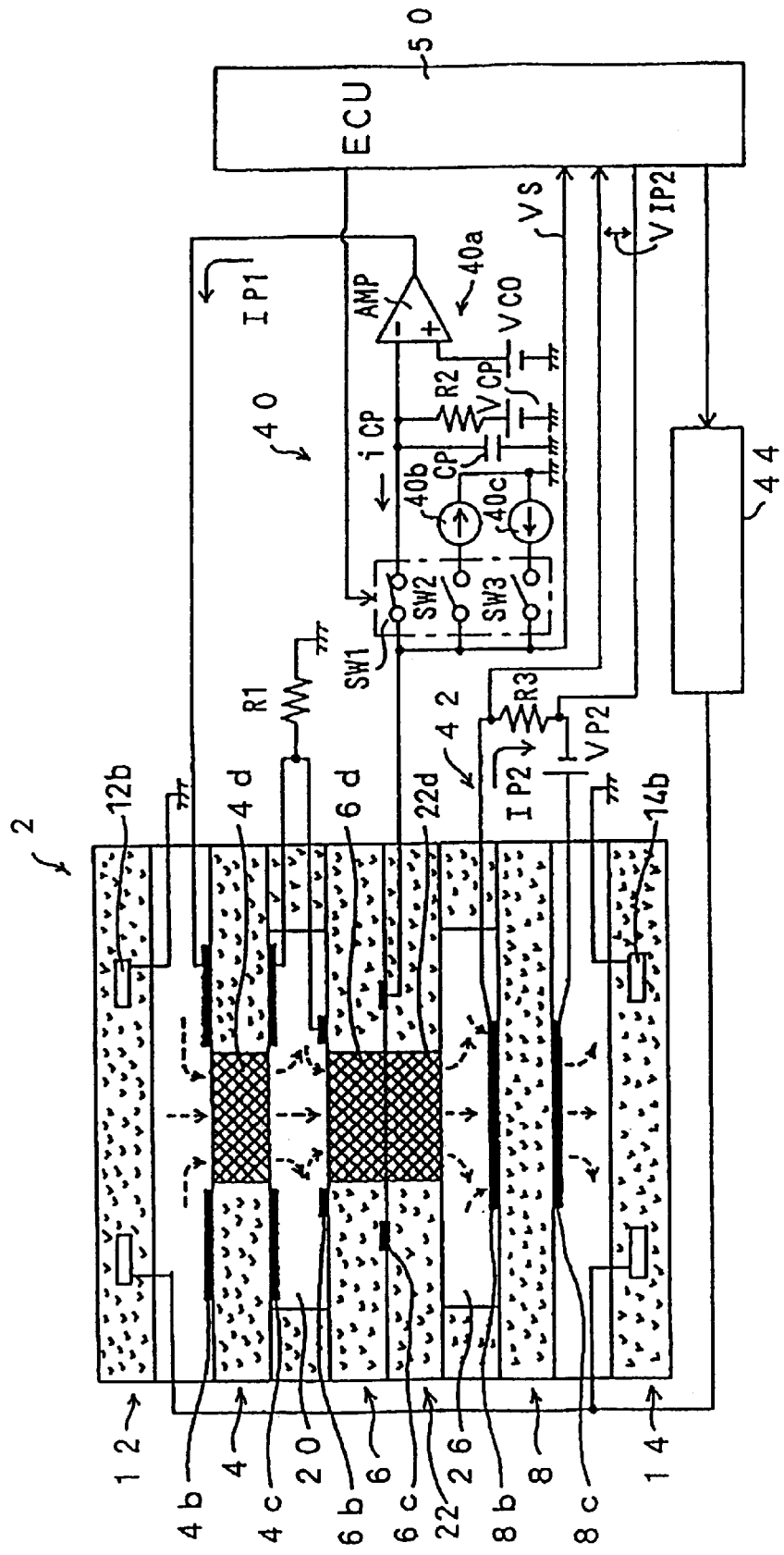
FIG. 2 is a schematic diagram showing the entire configuration of an $NO_x$ sensing apparatus employing the $NO_x$ sensor according to an embodiment of the present invention.

FIG. 1 shows the structure of an $NO_x$ sensor according to one embodiment of the present invention. FIG. 2 shows the entire configuration of an $NO_x$ sensing apparatus employing the $NO_x$ sensor.

As shown in FIG. 1, the $NO_x$ sensor 2 includes a first oxygen pumping cell (hereinafter referred to as a first pumping cell) 4, an oxygen concentration measuring cell (hereinafter referred to as a Vs cell) 6, a second oxygen pumping cell (hereinafter referred to as a second pumping cell) 8, and a pair of heaters 12 and 14 for heating the cells.

The first pumping cell 4 includes a sheet-like solid electrolyte layer 4a and rectangular porous electrodes 4b and 4c formed on both sides of the solid electrolyte layer 4a. Lead portions 4b1 and 4c1 extend from the porous electrodes 4b and 4c, respectively. Furthermore, a round hole is formed in the solid electrolyte layer 4a in such manner as to penetrate the porous electrodes 4b and 4c at the central portions thereof. The thus formed round hole is filled with a porous filler comprising, for example, alumina to thereby form a diffusion controlling layer 4d.

The Vs cell 6 includes a sheet-like solid electrolyte layer 6a similar to the solid electrolyte layer 4a of the first pumping cell 4 and circular porous electrodes 6b and 6c formed on both sides of the solid electrolyte layer 6a. Lead portions 6b1 and 6c1 extend from the porous electrodes 6b and 6c, respectively. Furthermore, a round hole is formed in the solid electrolyte layer 6a in such manner as to penetrate the porous electrodes 6b and 6c at the central portions thereof. The thus formed round hole is filled with a porous filler comprising, for example, alumina to thereby form a diffusion controlling layer 6d.

The porous electrodes 4b and 4c of the first pumping cell 4 and the porous electrodes 6b and 6c of the Vs cell 6 are located on the solid electrolyte layers 4a and 6a, respectively, such that their centers are aligned with each other. Accordingly, when the first pumping cell 4 and the Vs cell 6 are arranged as a laminate, the diffusion controlling layers 4d and 6d face each other. The circular porous electrodes 6b and 6c of the Vs cell 6 are arranged around the diffusion controlling layer 6d and have a size smaller than that of the rectangular porous electrodes 4b and 4c of the first pumping cell 4. Particularly, the porous electrode 6b located on the side of the first pumping cell 4 is formed within a very narrow range around the periphery of the diffusion controlling layer 6d in order to accurately detect the amount of oxygen flowing into the diffusion controlling layer 6d.

An insulation film 6e comprising zirconia or the like is formed on both surfaces of the Vs cell 6 so as to cover the lead portions 6b1 and 6c1 from the outside in order to prevent current leakage from the lead portions 6b1 and 6c1 and to accurately detect the amount of oxygen flowing into the diffusion controlling layer 6d. Furthermore, a leakage resistance portion 6f is formed between the lead portions 6b1 and 6c1 in order to leak part of the pumped out oxygen from the side of the porous electrode 6c to the side of the porous electrode 6b.

The first pumping cell 4 and the Vs cell 6 are arranged in a laminate with a solid electrolyte layer 18 interposed therebetween. The solid electrolyte layer 18 has the same shape as that of the solid electrolyte layers 4a and 6a. The solid electrolyte layer 18 has a rectangular opening formed therein in a position corresponding to the porous electrodes 4c and 6b and has a size greater than that of the porous electrode 4c. The thus formed rectangular opening serves as a first measurement space 20.

Also, a solid electrolyte layer 22, which has the same shape as that of the solid electrolyte layers 4a and 6a, is disposed on the Vs cell 6 on the side of the porous electrode 6c. The solid electrolyte layer 22 has a round hole formed therein in a position corresponding to the diffusion controlling layer 6d of the Vs cell 6. The thus formed round hole is filled with a porous filler comprising alumina or the like to thereby form a diffusion controlling layer 22d.

As in the first pumping cell 4, the second pumping cell 8 includes a sheet-like solid electrolyte layer 8a and rectangular porous electrodes 8b and 8c formed on both sides of the solid electrolyte layer 8a. Lead portions 8b1 and 8c1 extend from the porous electrodes 8b and 8c, respectively. The second pumping cell 8 and the solid electrolyte layer 22 are arranged in layers with a solid electrolyte layer 24 interposed therebetween. The solid electrolyte layer 24 is formed in the same manner as the solid electrolyte layer 18. As a result, a rectangular opening formed in the solid electrolyte layer 24 serves as a second measurement space 26.

Heaters 12 and 14 are placed on opposite sides of the above described laminate of the first pumping cell 4, the Vs cell 6, and the second pumping cell 8, namely, outside the first pumping cell 4 and the second pumping cell 8, respectively, such that a predetermined gap is formed between each of the heaters 12 and 14 and the laminate via spacers 28 and 29.

The heater 12 (14) includes heater substrates 12a and 12c (14a and 14c) having a shape similar to that of the solid electrolyte layers 4a, 6a, . . . , a heater wiring 12b (14b), and a lead portion 12b1 (14b1) extending from the heater wiring 12b (14b). The heater wiring 12b (14b) and the lead portion 12b1 (14b1) are interposed between the heater substrates 12a and 12c (14a and 14c). The spacer 28 (29) is interposed between the heater 12 (14) and the first pumping cell 4 (second pumping cell 8) so that the heater 12 (14) faces the porous electrode 4b (8c) of the first pumping cell 4 (second pumping cell 8) with a gap formed therebetween.

Typical examples of the solid electrolyte constituting the solid electrolyte layers 4a, 6a, . . . include a solid solution of zirconia and yttria and a solid solution of zirconia and calcia. Other examples of the solid electrolyte include a solid solution of hafnia, a solid solution of a perovskite oxide, and a solid solution of a trivalent metal oxide. The porous electrodes provided on the surfaces of the solid electrolyte layers 4a, 6a, and 8a are preferably formed of platinum or rhodium having a catalytic function or alloys thereof. Known methods of forming such porous electrodes include a thick film forming method and a thermal spraying method. The thick film forming method includes the steps of: mixing platinum powder and powder of the same material as that of the solid electrolyte layers to obtain a paste; screen printing the paste onto a solid electrolyte layer; and sintering the solid electrolyte layer. The diffusion controlling layers 4d, 6d, and 22d are preferably formed of ceramics having fine through holes or porous ceramics.

The heater wirings 12b and 14b of the heaters 12 and 14, respectively, are preferably formed of a composite material of ceramics and platinum or a platinum alloy. The lead portions 12b1 and 14b1 are preferably formed of platinum or a platinum alloy in order to reduce an electric loss therein by reducing their resistance. The heater substrates 12a, 12b, 14a and 14c and the spacers 28 and 29 may be formed of alumina, spinel, forsterite, steatite, zirconia, or the like.

Particularly preferably, the heater substrates and spacers are formed of zirconia because the heaters and pumping cells can be concurrently united by sintering to thereby facilitate the manufacture of the $NO_x$ sensor 2. In this case, an insulation layer (formed of alumina or the like) is interposed between the heater substrate 12a (12c) and the heater wiring 12b including the lead portion 12b1 and between the heater substrate 14a (14c) and the heater wiring 14b including the lead portion 14b1.

When the heater substrates are formed of alumina, the spacers are preferably formed of a porous material in order to prevent cracking which would otherwise occur during sintering of the heater substrates and the pumping cells due to differences in the respective coefficients of contraction or thermal expansion. Alternatively, the heaters and the pumping cells may be sintered separately, and then they may be bonded using cement or a like inorganic material serving as both a spacer and a bonding material.

As shown in FIG. 2, an $NO_x$ sensing apparatus employing the $NO_x$ sensor 2 having the above-described structure for measuring the $NO_x$ concentration includes: a drive circuit 40 for applying current to the first pumping cell 4 and Vs cell 6 of the $NO_x$ sensor 2 and for switching one current application path to the other; a sensing circuit 42 for detecting current (second pumping current) $I_{P2}$ which flows to the second pumping cell 8 of the $NO_x$ sensor 2 when a constant voltage is applied to the second pumping cell 8; a heater energizing circuit 44 for heating the cells 4, 6 and 8 by applying current to the heaters 12 and 14 of the $NO_x$ sensor 2; and an electronic control unit (hereinafter referred to as an ECU) 50, which includes a microcomputer, for driving and controlling the drive circuit 40 and the heater energizing circuit 44, and for calculating the concentration of $NO_x$ contained in a measurement gas based on a detection signal $V_{IP2}$ issued from the sensing circuit 42.

As shown in FIG. 2, the porous electrode 4c of the first pumping cell 4 and the porous electrode 6b of the Vs cell 6, both of which are located on the side of the first measurement space 20, are grounded via a resistor R1. The other porous electrodes 4b and 6c are connected to the drive circuit 40.

The drive circuit 40 includes a control section 40a which, in turn, includes a resistor R2 and a differential amplifier AMP. A constant voltage $V_{CP}$ is applied to one end of the resistor R2, and the other end of the resistor R2 is connected to the porous electrode 6c of the Vs cell 6 via a switch SW1. The negative input terminal of the differential amplifier AMP is connected to the porous electrode 6c of the Vs cell 6 via the switch SW1 and to one end of a capacitor Cp. A reference voltage $V_{C0}$ is applied to the positive input terminal of the differential amplifier AMP. The output terminal of the differential amplifier AMP is connected to the porous electrode 4b of the first pumping cell 4. The other end of the capacitor Cp is grounded.

When the switch SW1 is in the ON state, the control section 40a operates in the following manner.

First, a constant small current $i_{CP}$ is supplied to the Vs cell 6 via the resistor R2 to thereby pump out oxygen from the first measurement space 20 into the porous electrode 6c. Because the porous electrode 6c is blocked by the solid electrolyte layer 22 and communicates with the porous electrode 6b via the leakage resistance portion 6f, the concentration of oxygen contained in the blocked space of the porous electrode 6c is maintained at a constant level by applying the small current $i_{CP}$ to the Vs cell 6. Thus, the blocked space serves as an internal reference oxygen source.

When the porous electrode 6c of the Vs cell serves as an internal reference oxygen source, an electromotive force is generated in the Vs cell 6 in accordance with the difference in oxygen concentration between the first measurement space 20 and the internal reference oxygen source. As a result, a voltage Vs generated on the side of the porous electrode 6c corresponds to the concentration of oxygen contained in the first measurement space 20. Because the voltage Vs is applied to the input of the differential amplifier AMP, the differential amplifier AMP outputs a voltage in accordance with the deviation of the input voltage from the reference voltage $V_{C0}$ ($V_{C0}$—input voltage). The output voltage is applied to the porous electrode 4b of the first pumping cell 4.

As a result, a current $I_{P1}$ (hereinafter referred to as first pumping current $I_{P1}$) flows to the first pumping cell 4. By controlling the first pumping current $I_{P1}$, a constant electromotive force is generated in the Vs cell 6. That is, the control section 40a controls the pumping out of oxygen from the first measurement space 20 such that a predetermined amount of oxygen is pumped out from the first measurement space 20 into the second measurement space 26 via the diffusion controlling layers 6d and 22d serving as the second diffusion controlling layer.

The thus controlled amount of oxygen flowing from the first measurement space 20 into the second measurement space 26 is set to substantially zero (theoretically, a partial pressure of about $10^{-9}$ atm). The reference voltage VC0 which determines the amount of oxygen flowing from the first measurement space 20 into the second measurement space 26 is set at approximately 450 mV.

The drive circuit 40 further includes a constant current circuit 40b and a constant current circuit 40c. The constant current circuit 40b is connected to the porous electrode 6c of the Vs cell 6 via a switch SW2 and causes a constant current to flow between the porous electrodes 6b and 6c in a direction opposite that of the small current $i_{CP}$. The constant current circuit 40c is connected to the porous electrode 6c of the Vs cell 6 via a switch SW3 and causes a constant current to flow between the porous electrodes 6b and 6c in the same direction as that of the small current $i_{CP}$.

The constant current circuits 40b and 40c are adapted to detect the internal resistance $R_{VS}$ of the Vs cell 6. To allow the ECU 50 to detect the internal resistance $R_{VS}$ of the Vs cell 6 by supplying a constant current to the Vs cell 6, the voltage Vs generated on the side of the porous electrode 6c is input to the ECU 50. The constant current circuits 40b and 40c supply a constant current of the same value in opposite directions. The value of the constant current is greater than that of the small current $i_{CP}$, which is supplied to the Vs cell 6 via the resistor R2.

The switches SW1, SW2 and SW3 provided between the porous electrode 6c of the Vs cell 6 and the control section 40a and the constant current circuits 40b and 40c, respectively, are turned ON or OFF in accordance with a control signal issued by the ECU 50. In the normal mode where the $NO_x$ concentration is determined by means of the control section 40a, only the switch SW1 is turned ON. Only when the internal resistance $R_{VS}$ of the Vs cell 6 is to be detected, the switch SW1 is turned OFF, and the switches SW2 and SW3 are sequentially turned ON in this order.

A constant voltage $V_{P2}$ is applied between the porous electrodes 8b and 8c of the second pumping cell 8 of the $NO_x$ sensor 2 via a resistor R3, which is a component of the sensing circuit 42 and serves as a constant voltage application means. The constant voltage $V_{P2}$ is applied to the second pumping cell 8 in a polarity such that the porous electrodes 8c and 8b become a positive electrode and a negative electrode, respectively. As a result, current flows from the porous electrode 8c to the porous electrode 8b to thereby pump out oxygen from the second measurement space 26. The constant voltage $V_{P2}$ is set at a voltage, for example 450 mV, such that the $NO_x$ component contained in the measurement gas flowing from the first measurement space 20 into the second measurement space via the diffusion controlling layers 6d and 22d is decomposed in the second measurement space, and the resulting oxygen component is pumped out from the measurement gas.

The resistor R3 is adapted to convert the second pumping current $I_{P2}$ flowing through the second pumping cell 8 as a result of applying the constant voltage $V_{P2}$ to a voltage $V_{IP2}$, and is adapted to input the voltage $V_{IP2}$ to the ECU 50 as a detection signal corresponding to the second pumping current $I_{P2}$.

In the $NO_x$ sensing apparatus having the above described configuration, by turning switch SW1 ON and switches SW2 and SW3 OFF, the control section 40a can control the amount of oxygen contained in the measurement gas at substantially zero when the measurement gas flows from the first measurement space 20 into the second measurement space 26 via the diffusion controlling layers 6*d* and 22*d* (second diffusion controlling layer). The measurement gas initially flows into the first measurement space 20 via the diffusion controlling layer 4*d* (first diffusion controlling layer). Accordingly, the second pumping current $I_{P2}$ flowing through the second pumping cell 8 varies in accordance with the $NO_x$ concentration, while the concentration of oxygen contained in an ambient measurement gas hardly affects the second pumping current $I_{P2}$. Thus, by reading the detection signal $V_{IP2}$ corresponding to the second pumping current $I_{P2}$, and carrying out a predetermined computation based on the read signal, the ECU 50 can determine the concentration of $NO_x$ contained in the measurement gas from the detection signal $V_{IP2}$ (in other words, the second pumping current $I_{P2}$).

In order to accurately measure the $NO_x$ concentration, the temperature of the cells 4, 6 and 8, and particularly the temperature of the Vs cell 6 adapted to detect the concentration of oxygen contained in the first measurement space 20, is preferably controlled at a constant value. Thus, the amount of current applied to the heaters 12 and 14 by the heater energizing circuit 44 must be controlled such that the temperature of the Vs cell 6 achieves a target value. To attain this end, the ECU 50 carries out heater energizing control processing at predetermined intervals T0 as well as $NO_x$ concentration measuring processing. In the $NO_x$ concentration measuring processing, the ECU 50 turns the switch SW1 ON and the switches SW2 and SW3 OFF, and then reads the detection signal $V_{IP2}$ corresponding to the second pumping current $I_{P2}$ in order to measure the concentration of $NO_x$ contained in the measurement gas. In the heater energizing control processing, the ECU 50 turns the switch SW1 OFF and the switches SW2 and SW3 ON/OFF in order to detect the sensor temperature based on the internal resistance $R_{VS}$ of the Vs cell 6, and controls the amount of current supplied from the heater energizing circuit 44 to the heaters 12 and 14 such that the detected sensor temperature achieves a target value (for example, 850° C.)

Figure 3:
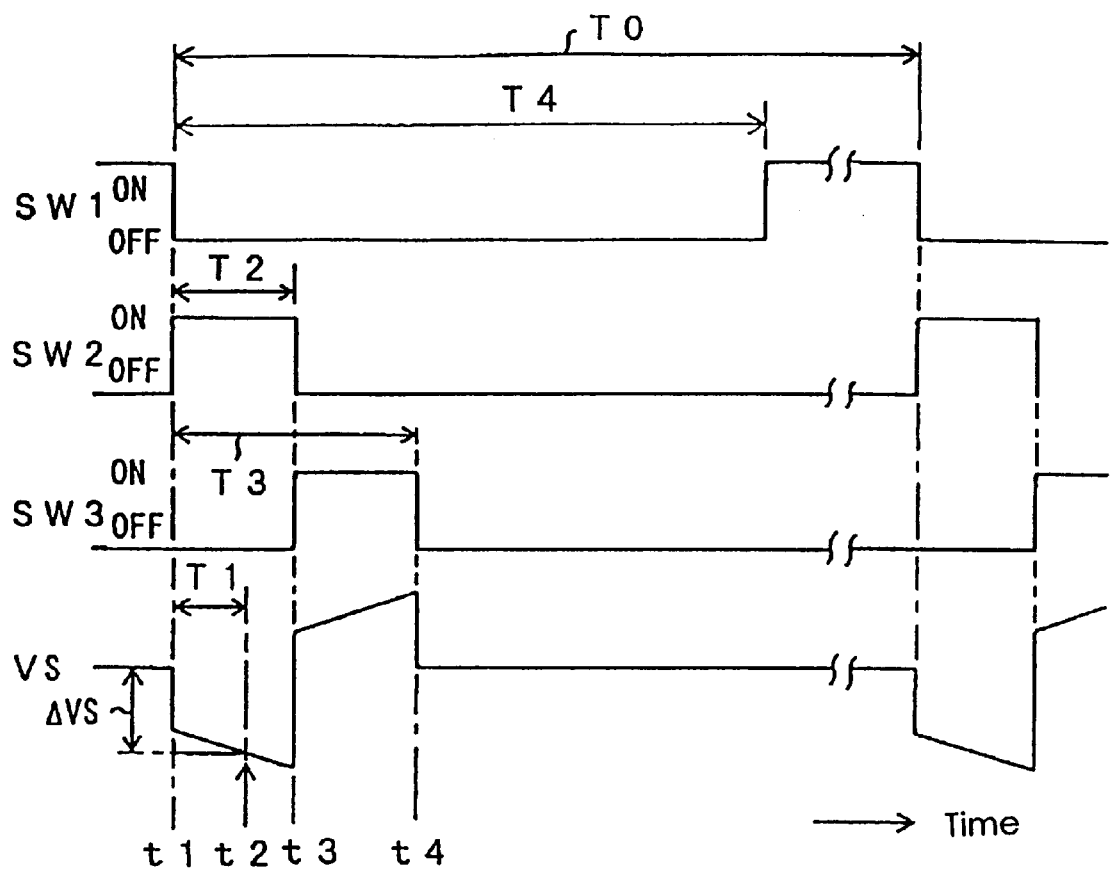
FIG. 3 is a timing chart in accordance with the present invention showing a heater energizing control operation as carried out by an ECU (electronic control unit) for controlling the sensor temperature.

That is, as shown in FIG. 3, upon starting the heater energizing operation control processing (at time t1), the ECU 50 reads the voltage Vs generated by the porous electrode 6*c* of the Vs cell 6 and turns the switch SW1 OFF and the switch SW2 ON, to thereby cause a constant current to flow in the Vs cell 6 in a direction opposite that of the small current $i_{CP}$. Subsequently, after the elapse of a predetermined time T1 (for example, 60 μsec), i.e., at time t2, the ECU 50 reads the voltage Vs again. After the elapse of a predetermined time T2 (for example, 100 μsec) of the control processing, i.e., at time t3, the ECU 50 turns the switch SW2 OFF and the switch SW3 ON, to thereby cause a constant current to flow in the Vs cell 6 in the same direction as that of the small current $i_{CP}$ (i.e., in a direction pumping out oxygen from the first measurement space 20 into a blocked space). Then, after the elapse of a predetermined time T3 (for example, 200 μsec) of the control processing, i.e., at time t4, the ECU 50 turns the switch SW3 OFF. Furthermore, after the elapse of a predetermined time T4 (for example, 500 μsec) of the control processing, the ECU 50 turns the switch SW1 ON, thus returning to the $NO_x$ concentration measuring processing.

During execution of the heater energizing operation control processing, the ECU 50 calculates the internal resistance $R_{VS}$ of the Vs cell 6 from the differential voltage $\Delta Vs$ between the voltage Vs generated by the porous electrode 6*c* as detected at time t1 and at time t2. The ECU 50 controls the amount of current supplied from the heater energizing circuit 44 to the heaters 12 and 14 such that the calculated internal resistance $R_{VS}$ achieves a target value. As a result, the amount of current supplied to the heaters 12 and 14 is controlled such that the internal resistance $R_{VS}$ of the Vs cell 6 (i.e., the sensor temperature) is maintained at a constant value. Accordingly, the temperature of $NO_x$ sensor 2 becomes constant.

As described above, in the $NO_x$ sensing apparatus of the present embodiment, the porous electrode 6*b* of the Vs cell 6 located on the side of the first pumping cell 4 is formed within a very narrow range along the periphery of the diffusion controlling layer 6*d*. Accordingly, the amount of oxygen flowing from the first measurement space 20 into the second measurement space 26 can be accurately measured. Also, when the $NO_x$ concentration is to be measured, the first pumping current $I_{P1}$ is controlled such that an output voltage from the Vs sensor 6 becomes the reference voltage $V_{CO}$. As a result, the amount of oxygen flowing from the first measurement space 20 into the second measurement space 26 becomes substantially zero.

Thus, according to the present invention, the $NO_x$ concentration can be accurately determined from the second pumping current $I_{P2}$ without being affected by the concentration of oxygen contained in the measurement gas. Also, because there is no need to compensate the $NO_x$ concentration as determined from the second pumping current $I_{P2}$ in accordance with the concentration of oxygen contained in the measurement gas, the sensing apparatus can be simply configured.

In the above embodiment, the diffusion controlling layer (first diffusion controlling layer) 4*d* is formed at the center of the electrodes 4*b* and 4*c* of the first pumping cell 4 so as to face the heater 12 (specifically, the center of the heater wiring 12*b*). However, for example, as shown in FIGS. 4 and 5, diffusion controlling layers 20*a* and 20*b* serving as the first diffusion controlling layer may be formed at the side portions of the solid electrode layer 18 which defines the first measurement space 20, to thereby pump in the measurement gas through the side portions of the $NO_x$ sensor 2.

Figure 6:
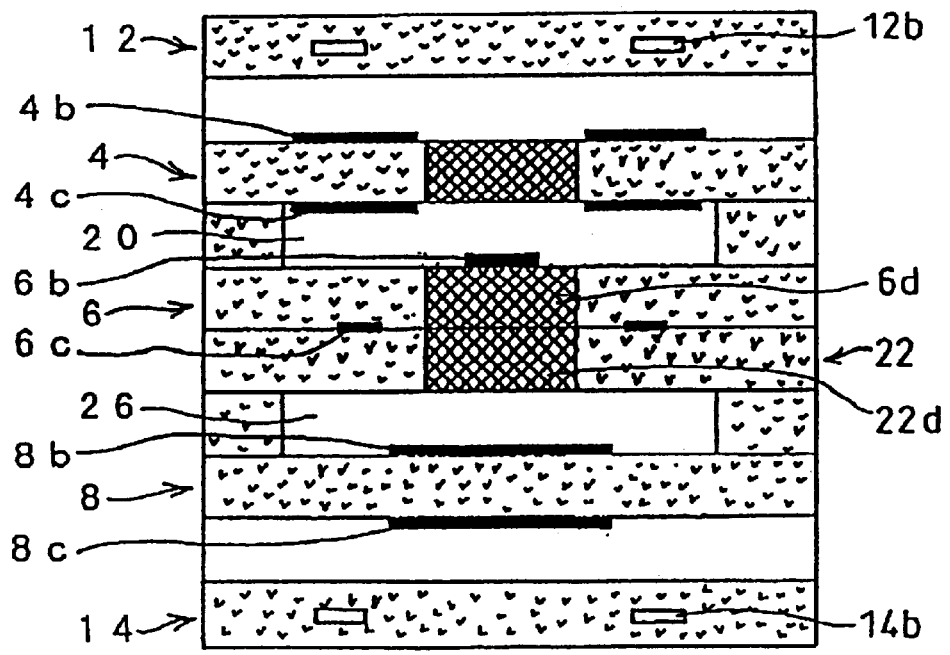
FIG. 6 is a sectional view showing the electrode arrangement of an $NO_x$ sensor in which the electrode located on the side of a first measurement space constituting a Vs cell is formed on a second diffusion controlling layer.

Also, in the above embodiment, the porous electrode 6*b* of the Vs cell 6 located on the side of the first pumping cell 4 is formed around the periphery of the diffusion controlling layer 6*d* in order to accurately detect the amount of oxygen flowing from the first measurement space 20 into the second measurement space 26. However, for example, as shown in FIG. 6, the porous electrode 6*b* in a yet further preferred embodiment may be formed on the diffusion controlling layer 6*d*. In this case, in order to generate a voltage between the electrodes 6*b* and 6*c* in accordance with the amount of oxygen flowing into the second measurement space 26, the diffusion controlling layer 6*d* must be formed of a porous solid electrolyte (zirconia or the like) capable of controlling diffusion of a measurement gas.

Figure 4:
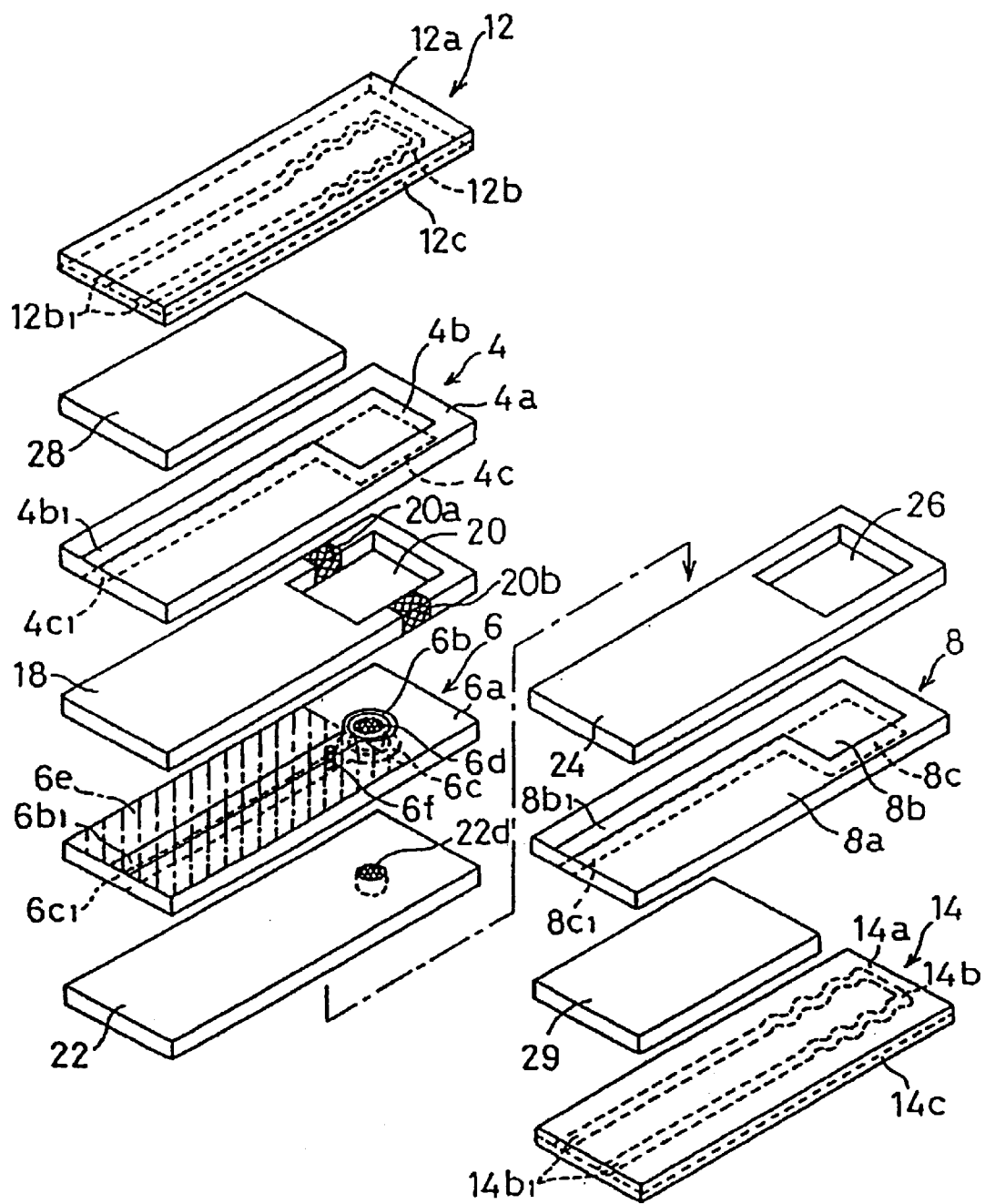
FIG. 4 is an exploded perspective view showing the structure of an $NO_x$ sensor in which first diffusion controlling layers are provided at opposing side edges of the sensor.
Figure 5:
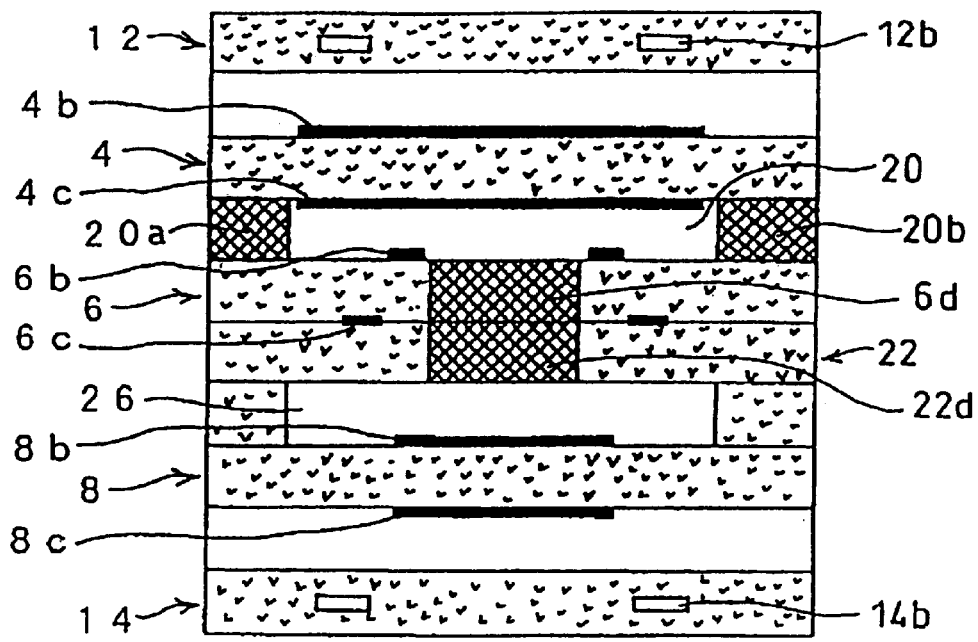
FIG. 5 is a sectional view showing the electrode arrangement of the $NO_x$ sensor of FIG. 4.

Except for the above-noted portions, the $NO_x$ sensor shown in FIGS. 4–6 has a structure similar to that of the $NO_x$ sensor 2 shown in FIGS. 1 and 2. Thus, a detailed description of the $NO_x$ sensor of FIGS. 4–6 is omitted.

EXAMPLES

Next, the degree of improvement in $NO_x$ concentration measurement accuracy is shown below as a function of the location of the porous electrode 6*b* of the Vs cell 6, and specifically a location around the periphery of the diffusion controlling layer 6*d* or on the diffusion controlling layer 6*d*, by reference to the following experimental results. However, the present invention should not be construed as being limited thereto.

Figure 7:
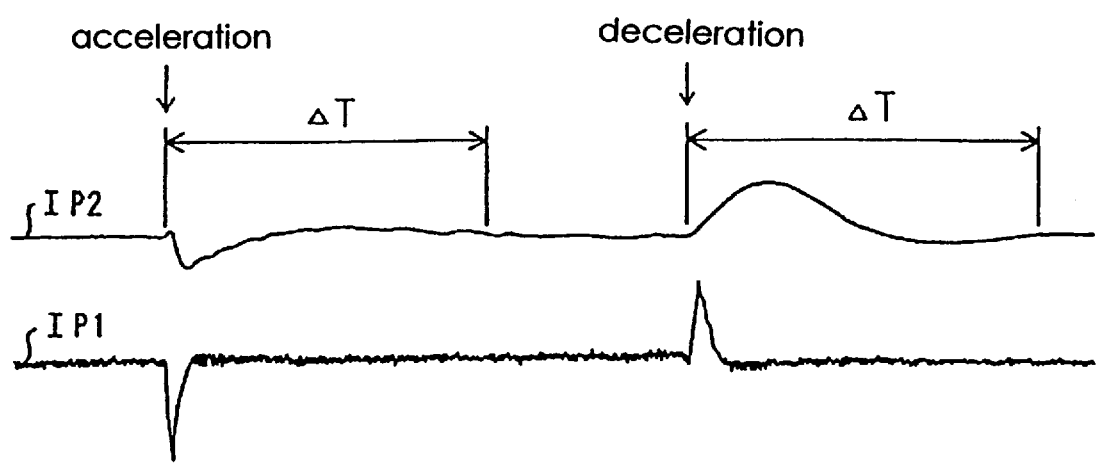
FIG. 7 is a timing chart showing the variation in the measured $NO_x$ concentration (second pumping current) in accordance with the transient fluctuation of a measurement gas.

The experiment involved two types of $NO_x$ sensors, namely, the $NO_x$ sensor of the first embodiment shown in FIGS. 1 and 2 (an $NO_x$ sensor in which the first diffusion controlling layer faces the heater 12), and the $NO_x$ sensor of the second embodiment shown in FIGS. 4 and 5 (an $NO_x$ sensor in which the first diffusion controlling layer is located at the side edges of the $NO_x$ sensor). For each type were manufactured an $NO_x$ sensor including a porous electrode 6b having a diameter of 2 mm, an $NO_x$ sensor including a porous electrode 6b having a diameter of 1 mm, and an $NO_x$ sensor including a porous electrode 6b formed on the second diffusion controlling layer as shown in FIG. 6. The thus manufactured six kinds of $NO_x$ sensors were attached to the exhaust pipe of an internal combustion engine. The average time $\Delta T$ that elapsed until the measured $NO_x$ concentration (i.e., the measured second pumping current $I_{P2}$) became stable was measured during acceleration and deceleration of the internal combustion engine (FIG. 7).

As a result, as shown in Table 1, among the $NO_x$ sensors in which the porous electrode 6b was formed around the periphery of the diffusion controlling layer 6d, the $NO_x$ sensor having the smaller sized porous electrode 6b exhibited a shorter $\Delta T$ under transient conditions of the measurement gas (under transient conditions, both the temperature and oxygen concentration may vary). Also, the $NO_x$ sensors in which the porous electrode 6b was formed on the diffusion controlling layer 6d exhibited a shorter $\Delta T$ as compared with the $NO_x$ sensors in which the porous electrode 6b was formed around the periphery of the diffusion controlling layer 6d. This is because when the porous electrode 6b is located closer to the diffusion controlling layer 6d, the amount of oxygen flowing from the first measurement space 20 into the second measurement space 26 can be determined more accurately. As a result, the $NO_x$ concentration measurement is less affected by variations in the concentration of oxygen contained in the measurement gas.

Also, as seen from Table 1, the $NO_x$ sensors of the first embodiment, in which the first diffusion controlling layer faces the heater 12, exhibited a shorter $\Delta T$ under transient measurement gas conditions as compared with the $NO_x$ sensors of the second embodiment, in which the first diffusion controlling layer was located at the side edges of the $NO_x$ sensor. This is because by having the first diffusion controlling layer and the heater 12 face each other, the measurement gas flowing into the first measurement space 20 can be heated by the heater 12. As a result, the $NO_x$ concentration measurement is less affected by variations in the temperature of the measurement gas.

TABLE 1

(Measurement of fluctuation time $\Delta T$ of $I_{P2}$ under transient conditions)

| Porous electrode 6b | First embodiment | Second embodiment |
| --- | --- | --- |
| Diameter: 2 mm | 40 sec | 65 sec |
| Diameter: 1 mm | 20 sec | 35 sec |
| Located on second diffusion controlling layer | 12 sec | 20 sec |

Figure 8A:
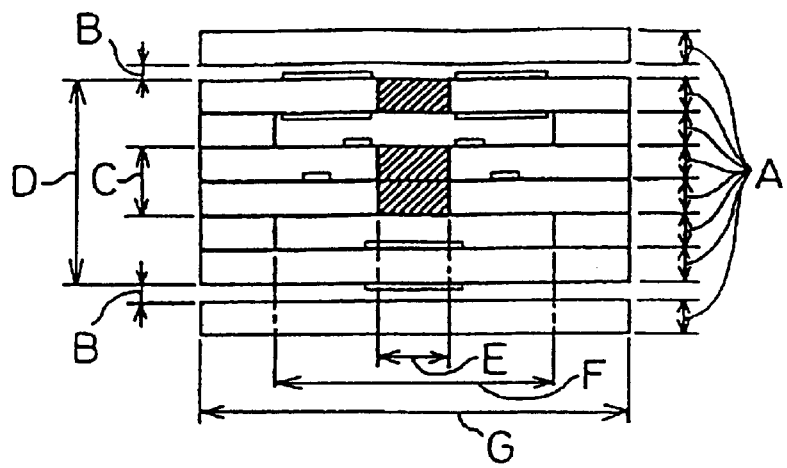
FIGS. 8A–8C are views showing the dimensional relationships of the $NO_x$ sensors used in the Examples.

As shown in FIG. 8A, the dimensions of the $NO_x$ sensors of the first embodiment as used in the above experiment were as follows: The thickness A of the heaters 12 and 14 and the thickness A of the solid electrolyte layers 4a, 6a, 8a, 18, 22 and 24 that formed the first pumping cell 4, the Vs cell 6, the second pumping cell 8, the first measurement space 20, the diffusion controlling layer 22d and the second measurement space 26, respectively, were each 0.25 mm. The thickness B of the spacers 28 and 29 that determine the gap between the heater 12 and the first pumping cell 4 and between the heater 14 and the second pumping cell 8 was 0.1 mm. Accordingly, the thickness D of the $NO_x$ sensor body excluding the heaters 12 and 14 was 1.5 mm. Also, the thickness C of the second diffusion controlling layer comprising the diffusion controlling layers 6d and 22d was 0.5 mm.

Figure 8B:
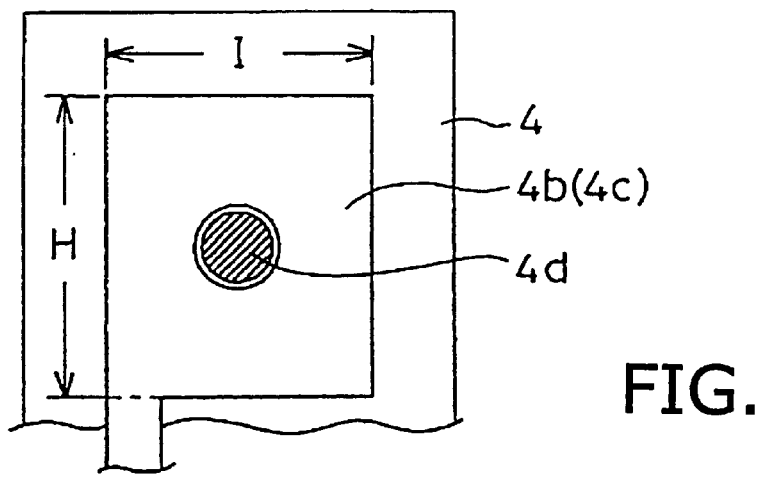

The diameter of the diffusion controlling layers 4d, 6d and 22d was 0.5 mm; the width F of the first and second measurement spaces 20 and 26, respectively, as measured in the lateral direction of the $NO_x$ sensor was 2.5 mm; and the width G of the $NO_x$ sensor was 3.5 mm. As shown in FIG. 8B, the width I of the porous electrodes 4b and 4c formed around the diffusion controlling layer (first diffusion controlling layer) was 2.4 mm; and the length H of the porous electrodes 4b and 4c as measured in the longitudinal direction of the $NO_x$ sensor was 3.0 mm.

Figure 8C:
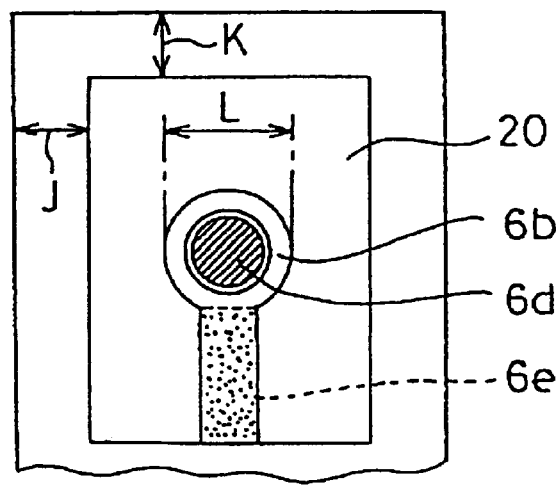

As shown in FIG. 8C, the rectangular hole serving as the first measurement space 20 was formed in the solid electrolyte layer 18 such that distance K from the top end of the $NO_x$ sensor was 0.5 mm and the distance J from either side edge of the $NO_x$ sensor was 0.5 mm. The porous electrode 6b formed around the periphery of the diffusion controlling layer 6d had a diameter L of 2 mm or 1 mm. The porous electrode 6b formed on the diffusion controlling layer 6d had a diameter of 0.4 mm.

The $NO_x$ sensors of the second embodiment used in the experiment had dimensions identical to those of the $NO_x$ sensors of the first embodiment except for the following dimensions. The diffusion controlling layers 20a and 20b (first diffusion controlling layer) formed at the side portions of the $NO_x$ sensor had a length of 1 mm as measured in the longitudinal direction of the $NO_x$ sensor. The porous electrodes 4b and 4c of the first pumping cell measured 2.4 mm×3.0 mm and were formed in a solid manner.

It should further be apparent to those skilled in the art that various changes in form and detail of the invention as shown and described above may be made. It is intended that such changes be included within the spirit and scope of the claims appended hereto.

What is claimed is:

1. An $NO_x$ sensor for measuring the $NO_x$ concentration of a measurement gas, comprising:

solid electrolyte layers arranged in the form of a laminate having a laminating direction, a first measurement space including a first oxygen pumping cell and an oxygen concentration measuring cell and communicating with the measurement gas via a first diffusion controlling layer, said first oxygen pumping cell comprising an oxygen ion conductive solid electrolyte and porous electrodes disposed on opposite surfaces of the oxygen ion conductive solid electrolyte layer, and said oxygen concentration measuring cell comprising an oxygen ion conductive solid electrolyte layer and porous electrodes disposed on opposite surfaces of the oxygen ion conductive solid electrolyte layer;

a second measurement space including a second oxygen pumping cell and communicating with said first measurement space via a second diffusion controlling layer, said second oxygen pumping cell comprising an oxygen ion conductive solid electrolyte layer and porous electrodes disposed on opposite surfaces of the oxygen ion conductive solid electrolyte layer;

wherein the electrode layers are arranged in the form of a laminate having a laminating direction, means for maintaining an output voltage of said oxygen concentration measuring cell at a constant value, which means comprises said first oxygen pumping cell for pumping cell for pumping oxygen from said first measurement space; and means for applying a constant voltage to said second oxygen pumping cell for pumping oxygen from said second measurement space, whereby the concentration of $NO_x$ contained in the measurement gas can be determined by measuring the current flowing through said second oxygen pumping cell; and wherein said oxygen concentration measuring cell is disposed in a position such that the amount of oxygen contained in the measurement gas flowing from said first measurement space into said second measurement space via said second diffusion controlling layer can be determined without being affected by the distribution of oxygen within said first measurement space; and wherein said second diffusion controlling layer comprises a porous solid electrolyte layer capable of controlling diffusion of the measurement gas, and the electrode of said oxygen concentration measuring cell located on the side of said first measurement space is formed on a portion of said second diffusion controlling layer; and wherein said second diffusion controlling layer at least partially overlaps said first diffusion controlling layer in the laminating direction of said laminate.

2. An $NO_x$ sensor for measuring the $NO_x$ concentration of a measurement gas, comprising:

a first measurement space including a first oxygen pumping cell and an oxygen concentration measuring cell, said first measurement space communicating with the measurement gas via a first diffusion controlling layer, said first oxygen pumping cell comprising an oxygen ion conductive solid electrolyte layer and porous electrodes disposed on opposite surfaces of the oxygen ion conductive solid electrolyte layer, and said oxygen concentration measuring cell comprising an oxygen ion conductive solid electrolyte layer and porous electrodes disposed on opposite surfaces of the oxygen ion conductive solid electrolyte layer; and a second measurement space including a second oxygen pumping cell and communicating with said first measurement space via a second diffusion controlling layer of a solid electrolyte material, said oxygen pumping cell comprising an oxygen ion conductive solid electrolyte layer and porous electrodes disposed on opposite surfaces of the oxygen ion conductive solid electrolyte layer;

wherein the solid electrolyte layers are arranged in the form of a laminate having a laminating direction, wherein the electrode of said oxygen concentration measuring cell located on the side of said first measurement space is formed on a portion of said second diffusion controlling layer; and wherein said second diffusion controlling layer at least partially overlaps said first diffusion controlling layer in the laminating direction of said laminate.

3. The $NO_x$ sensor as claimed in claim 2, wherein the solid electrolyte layers include at least one inner layer, the first measurement space is defined by a gap provided between the solid electrolyte layer constituting said first oxygen pumping cell and the at least one inner layer, and the second measurement space is defined by a gap provided between the solid electrolyte layer constituting said second oxygen pumping cell and the at least one inner layer; and wherein said at least one inner solid electrolyte layer includes an inner layer having a third diffusion controlling layer formed therein arranged between the solid electrolyte layer constituting the oxygen concentration measuring cell and the solid electrolyte layer constituting the second oxygen pumping cell, and the second measurement space is defined by a gap provided between the solid electrolyte layer constituting said second oxygen pumping cell and said inner solid electrolyte layer having the third diffusion controlling layer; and wherein said first, second and third diffusion controlling layers at least partially overlap each other in the laminating direction of said laminate.

* * * * *